United States Patent [19]
Anvari et al.

[11] Patent Number: 5,979,454
[45] Date of Patent: Nov. 9, 1999

[54] METHOD AND APPARATUS FOR CAUSING RAPID AND DEEP SPATIALLY SELECTIVE COAGULATION DURING THERMALLY MEDIATED THERAPEUTIC PROCEDURES

[75] Inventors: Bahman Anvari; Samuel B. Tanenbaum; Thomas E. Milner, all of Irvine; J. Stuart Nelson, Laguna Niguel, all of Calif.

[73] Assignee: The Regents of the University of California, Oakland, Calif.

[21] Appl. No.: 08/870,467

[22] Filed: Jun. 6, 1997

Related U.S. Application Data

[63] Continuation-in-part of application No. 08/441,930, May 15, 1995, Pat. No. 5,814,040.

[51] Int. Cl.$^6$ .................................................. A61N 5/06
[52] U.S. Cl. .............................................. 128/898; 606/9
[58] Field of Search ..................... 606/2, 9–12, 20–24; 607/88, 89; 128/898

[56] References Cited

U.S. PATENT DOCUMENTS

| | | | |
|---|---|---|---|
| 5,057,104 | 10/1991 | Chess | 606/9 |
| 5,344,418 | 9/1994 | Ghaffari | 606/9 |
| 5,814,040 | 9/1998 | Nelson et al. | 606/9 |

OTHER PUBLICATIONS

Anvari et al, "Dynamic Epidermal . . . Evaluations", Lasers in Medical Science, vol. 10, pp. 105–112, 1995.
Anvari et al, "Spatially Selective . . . Cooling", Applied Optics, vol. 35, No. 19, pp. 3314–3320, Jul. 1996.

*Primary Examiner*—Michael Peffley
*Attorney, Agent, or Firm*—Daniel L. Dawes

[57] ABSTRACT

Successful laser treatment of hemangiomas requires selective photocoagulation of subsurface targeted blood vessels without thermal damage to the overlying epidermis. An apparatus for in vivo exposure of laser radiation from a continuous Nd:YAG laser at 1064 nm delivers repetitive cryogen spurts, each having a duration of the order of milliseconds during continuous laser irradiation. Control of the cryogen spray cooling is achieved through monitoring of the radiometric surface temperature of the tissue site and either controlling the repetition rate of the cryogen spurts according to temperature or according to a threshold temperature of the irradiated surface and/or repetition rate of the cryogen spurts according to power density and the duration of continuous irradiation.

13 Claims, 5 Drawing Sheets

METHOD AND APPARATUS FOR CAUSING RAPID AND DEEP SPATIALLY SELECTIVE COAGULATION DURING THERMALLY MEDIATED THERAPEUTIC PROCEDURES

The present application is a continuation-in-part application of application Ser. No. 08/441,930, filed May 15, 1995 now issued as U.S. Pat. No. 5,814,040, which is incorporated herein by reference.

BACKGROUND OF THE INVENTION

1. Field of the Invention

The invention relates to an apparatus and methodology for thermally mediated therapeutic procedures, and in particular for selective coagulation of specific components in selected regions in a biological matrix, when using focused ultrasound or electromagnetic radiation, such as a laser or microwave radiation, to induce thermal injury to the tissue.

2. Description of the Prior Art

Various thermally mediated therapeutic procedures using microwave, infrared or visible light energy have been used to induce coagulation necrosis of certain tissue components while protecting superficial tissues from thermal injury. For example, successful laser treatment of dermatoses, such as port wine stain lesions, hemangiomas, and telangiectasias, is based on photocoagulation of blood vessels without inducing thermal injury to the overlaying epidermis and papillary dermis, which could result in skin-surface texture changing or scaring.

Cryogen spray cooling is a potentially effective method for protecting superficial tissues from thermal injury. By the application of a short duration spurt of cryogen in the order of milliseconds, rapid and selective cooling of tissues is possible. Superficial tissues are cooled while the temperature of deeper tissues remain unchanged. Evaporation of the cryogen on the surface provides a mechanism for rapid removal of heat from the tissue. For example, when tetrafluoroethane, having a boiling point of −26° C., is used as a cryogen, surface temperature drops of the order of 30–40° C. have been obtained within 5–100 milliseconds. Experimental results indicate that spray cooling the tissue, e.g. skin, with tetrafluoroethane just prior to laser irradiation can selectively cool the superficial layer, e.g. epidermis, and yet permit photocoagulation of deeper dilated structures, e.g. port wine stain blood vessels. Successful blanching of port wine stain lesions without either epidermal thermal injury or skin-surface textural changes have been reported when the skin is precooled with tetrafluoroethane immediately prior to flashlamp-pumped pulsed dye laser irradiation with a relatively high-light dosage of about 10 J/cm$^2$.

Surface cooling with ice or water has also been used as a method to prevent laser-induced thermal injury to the epidermis. Although this method has been shown effective in cooling skin, exposure time are too long (seconds) to reduce the temperature of the underlying targeted blood vessels. Consequently, incident laser energy is utilized ineffectively by first rewarming the blood vessels to their higher initial temperature before sufficient heat is generated to induce photocoagulation.

Some investigators have studied the effectiveness of delivering a short cryogen spurt, on the order of milliseconds, to selectively cool the epidermis without reducing temperature of the underlying targeted blood vessels. When used in conjunction with flashlamp pumped pulsed dye laser irradiation for treatment of vascular lesions, use of cryogen spray cooling has been demonstrated to prevent skin textural changes that result from thermally induced epidermal injury, while allowing blanching of port wine stains. In the absence of cryogen spray cooling, epidermal necrosis and subsequent skin pigmentation changes have been observed when treatments are administered with equivalent laser irradiation parameters.

The foregoing treatments have all been used for superficial dermal mediation, typically relating to hair removal, wrinkle treatment, and port wine stain removal. Laser Treatment without cooling has been practiced for tattoo removal. Hemangiomas are vascular tumors, characterized by rapid endothelial cell proliferation, which may infiltrate the entire dermis and extend several millimeters in depth. The depth and size of hemangiomas are far deeper than chromophores targeted for hair removal, wrinkle treatment, and port wine stain. Although laser irradiation has been used to induce photothermal destruction of hemangiomas, thermal damage to the epidermis and papillary dermis remain a serious concern. Therefore, what is needed is an apparatus and methodology whereby deep photocoagulation without thermal damage to the overlying epidermis can be successfully practiced.

BRIEF SUMMARY OF THE INVENTION

The invention is a method to induce deep tissue photocoagulation while protecting superficial tissues comprising the steps of: 1) continuously irradiating a selected tissue site to raise its temperature; 2) monitoring the temperature of the tissue site, e.g. tissue surface; 3) to allow concurrent cooling with repetitive cryogen spurts while irradiating. The cooling is pulsed during irradiation of the tissue site and for a predetermined time thereafter. The cryogen spurt repetition rate is based on the monitored temperature at the tissue site, a mathematically predetermined model, empirically determined in the laboratory, or determined according to clinical observation.

In the preferred embodiment the cooling is performed by spraying a cryogen onto the skin, but the invention specifically contemplates cooling by any means now known or later devised, including pulse cooling with cold plates supplied with pulsed cryogen. The surface temperature is preferably radiometrically monitored, but any other means now known or later devised could be substituted. In the preferred embodiment irradiating the tissue site is performed with a laser or maser. Again any form of energy delivery to raise the temperature of the deep tissues could be used, including incoherent radiative sources, microwaves and ultrasound.

The step of controlling the cryogen spray cooling comprises initiating the spurts whenever the monitored temperature exceeds a predetermined threshold condition. In a first embodiment, the pulsed cryogen spray cooling is pulsed at a rate or rates dependent upon a threshold condition determined by feedback of a biological parameter or a time derivative of a biological parameter, e.g. skin surface temperature, birefringence, optical properties, such as optical scattering or absorption of the skin or some region or structures in it.

In one embodiment, the control of the cryogen spray cooling is bimodally controlled. The pulse rate is controlled as a first function of time of laser irradiation during irradiation of the tissue site and is controlled by a second function of the time after laser irradiation. The form of the first and second functions in this bimodal or multimodal cooling protocol may be determined mathematically based on certain biophysical assumptions and models, empirically by laboratory established protocols, or clinically by physician judgment.

For example, in one mathematically determined cooling protocol, the first function is $C[1-P(\mu)]$ for $t \leq t_{irrad}$ and second function is $C[P(\mu^*)-P(\mu)]$ for $\geq t_{irrad}$ where $\mu^* = \mu \sqrt{\alpha(t-t_{irrad})}$, $P(\mu) = e^{(\mu^2)} \text{erfc}(\mu)$ where $\mu = \mu\sqrt{\alpha t}$, and $\mu$ is the effective attenuation, $\alpha$ is tissue thermal diffusivity and C is an empirical constant coefficient.

The invention is also defined as an apparatus for deep photocoagulation of tissue without thermal damage to superficial tissues comprising a source of radiation energy directed to a tissue site and a cooling device for selectively delivering a plurality of pulsed cooling spurts to the tissue site. A monitor measures temperature of the tissue site. A controller is coupled to the temperature monitor and to the cryogen delivery device for controlling the cryogen delivery in response to the monitored temperature of the tissue site.

In the illustrated embodiment the source of radiation is a continuous wave laser, namely a Nd:YAG operating at 1064 nm. The cooling device is a cryogenic spray cooling system which controllably generates and directs spurts of cryogenic fluid onto the surface of the tissue site. The temperature monitor is an infrared radiometer. The controller activates the cooling device to deliver a spurt of cryogen to the tissue site whenever the temperature monitor indicates the biological parameter or some measure of it, e.g. surface temperature, at the tissue site equals or exceeds a predetermined threshold condition. The cooling device delivers pulsed cryogenic spray cooling to the tissue site for a predetermined time period after radiation of the tissue site by the source of radiation. The cooling device is governed by the controller to deliver spurts of cryogen to the tissue site at a rate dependent upon the duration or irradiance at the tissue site and depending upon time since initiation of radiation.

The invention, now having been briefly summarized, can be better visualized by turning to the following drawings, wherein like elements are referenced by like numerals:

Figure 1:
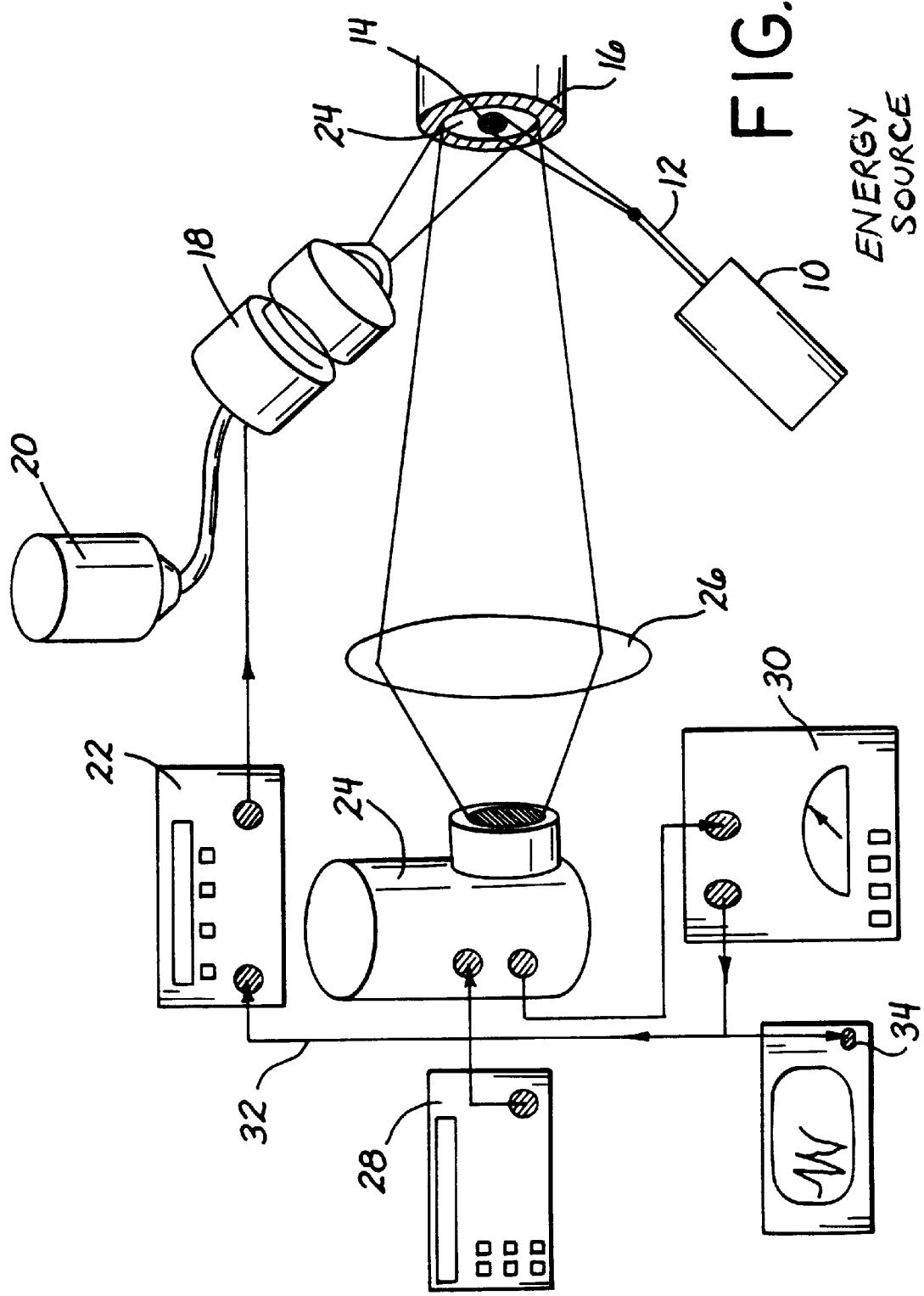
FIG. 1 is a simplified diagram of the apparatus for providing deep photocoagulation of tissue according to the invention.

The invention and its various embodiments as depicted in the foregoing drawings may now be better understood by turning to the following detailed description of the following embodiments:

DETAILED DESCRIPTION OF THE PREFERRED EMBODIMENTS

Successful laser treatment of hemangiomas requires selective photocoagulation of subsurface targeted blood vessels without thermal damage to the overlying epidermis. An apparatus for in vivo exposure of laser radiation from a continuous Nd:YAG laser at 1064 nm delivers repetitive cryogen spurts, each having a duration of the order of milliseconds during continuous laser irradiation. Control of the cryogen spray cooling is achieved through monitoring of the radiometric surface temperature of the tissue site and either controlling the repetition rate of the cryogen spurts according to temperature or according to a threshold temperature of the irradiated surface and/or repetition rate of the cryogen spurts according to time since initiation of irradiation and the length of continuous irradiation.

The use of repetitive milliseconds spurts of a cooling agent, such as tetrafluoroethane, difluoroethane, clorodifluoroethane and diclorodifluoroethane, applied to tissue during continuous irradiation with, for example, an Nd:YAG laser at 1064 nm is described below as the illustrated embodiment. Rapid temperature drops of the order of 30–40° C. can be achieved in the order of milliseconds. Because the tissue may be cooled so effectively, heating can be done much faster so photocoagulation can be achieved in a much shorter time, thus achieving better spatial selectivity. Specific predetermined regions in a biological matrix are preserved while targeted regions are coagulated. To achieve deep photocoagulation, tissues are radiated continuously. Millisecond spurts of cryogen are sprayed onto the tissue at specific times through a solenoid controlled valve. Cryogen spurts are delivered at a frequency determined by the thermal characteristics of the irradiated tissue site and irradiance of Nd:YAG, which frequency is variable both in time and with respect to the power density of the laser irradiation, while radiometric temperature measurements from the irradiated surface are monitored to determine if a thermal surface threshold condition is satisfied. By adjusting the spurt duration and the spurt application frequency as well as adjusting the irradiation parameters such as exposure time, intensity and power, regions of protected and photocoagulated tissue can be created in a controlled manner as described in connection with the in vivo model below.

The illustrated embodiment is the highly vascularized chicken comb. This model was chosen for its similarity to hemangiomas, since the histoanatomy is known to be analogous to that found in selected vascular birthmarks and has been extensively studied in the medical literature. It must be expressly understood that the invention is not limited to animal application, but specifically contemplates human use, and that any source of energy in addition to laser light may be used, such as microwave, ultrasound, radiofrequencies. Furthermore, cooling need not be by spray, cryogen or a contacting liquid as long as the thermal and heat specifications of the invention are practiced according to the teachings of the invention.

Seven adult female leghorn chickens were anesthetized by intravenously injecting 0.3 ml of ketamine and xylazine in a 9:1 volumetric ratio about 10–15 minutes prior to the beginning of each experiment. FIG. 1 diagramatically illustrates the apparatus used for laser irradiation and cryogen spray cooling. Laser light from a 1064 nm Nd:YAG laser 10 is coupled through a 600 micron core-diameter silica multimode optical fiber 12 directly onto a target spot 14 on comb surface 16. In the illustrated embodiment three ranges of power level, low, immediate and high, were selected as shown in Table I below.

TABLE I

Laser irradiation parameters used in the experiments.

| Power level | Delivered laser power, P (W) | Irradiation time, $t_{irrad(s)}$ | irradiance, E (J/mm$^2$) |
|---|---|---|---|
| Low | 5 | 20, 90, 135 | 2.6, 11.7, 17.5 |
| | 10 | 100 | 26 |
| | 15 | 30 | 11.7 |
| | 20 | 25 | 13 |
| Intermediate | 35 | 10, 20, 30 | 9.1, 18.2, 27.3 |
| | 40 | 15, 20, 30 | 15.6, 20.8, 31.2 |
| | 50 | 20 | 26 |
| High | 60 | 15, 20 | 23.4, 31.2 |
| | 70 | 15 | 27.3 |
| | 90 | 10, 15 | 23.4, 35.1 |

Chlorodifluoromethane (b. p. ~ 40° C.) was used as cryogen.
Diameter of laser irradiated spot was 7 mm in all experiments.

Irradiation times on the order of tens of seconds were used to achieve a large volume of photocoagulated tissue as shown in Table I. The diameter of the laser irradiated site 14 was maintained at approximately 7 millimeters in all experiments. Depending on the size of comb surface 16, 3–11 sites were irradiated with more comb areas allowing for fewer irradiation sites.

The irradiation and cryogen spray cooling parameters utilized in each comb 16 are summarized below in Table 2.

TABLE II

Laser irradiation and cryogen spray cooling (CSC) parameters used on each chicken comb.

| Comb number | Delivered laser power, P (W) | irradiation time, $t_{irrad(s)}$ | Spurt duration, τ (ms) | Euthanasia time (post experimental procedure) |
|---|---|---|---|---|
| 1 | 20 | 10 | 0– | 1 hour |
| | 35 | 10, 20 | 50 | |
| | 40 | 30 | 50 | |
| 2 | 40 | 20 | 50, 80 | 3 days |
| | 50 | 20 | 50, 80 | |
| | 60– | 20 | 50 | |
| 3 | 15 | 30 | 0 | 6 days |
| | 40 | 15, 20, 30 | 50, 80 | |
| | 60 | 15 | 70 | |
| | 70 | 15 | 80 | |
| | 90 | 10, 15 | 100 | |
| 4 | 5 | 20, 90, 135 | 50, 60 | 8 days |
| | 10 | 100 | 50 | |
| | 20 | 10, 25 | 0, 30, 50 | |
| | 35 | 20, 30 | 50, 80 | 21 days |

Chlorodifludromethane was used on chicken combs 1–5.

Chlorodifluoromethane, with a boiling point of approximately −40° C. was used as an exemplary cryogen on five chicken combs. Cryogen was sprayed on the comb 16 through an electronically controlled standard automobile fuel injection valve 18 coupled to a cryogen reservoir 20. Injection valve 18 was positioned approximately 4 cm from comb surface 16 at an angle of approximately 30 degrees from the normal to comb surface 16. Cryogen spurt durations were set by a programmable digital delay generator 22 coupled to solenoid valve 18. Spray durations ranged between 30 and 100 milliseconds as summarized in Table 2 above. Cooled site 24 of comb surface 16 was concentric with laser irradiated site 14 and extended around it, being about 10 millimeters in diameter. No thermally induced injury was observed on comb surface 16 from the cryogen spray.

In the illustrated embodiment, a radiometric measurement of the surface temperature at the center of laser irradiated site 14 was used to trigger delivery of the cryogen spurts. Radiometric infrared emission measurement from comb surface 16 was made by means of an HgCdTe detector 24 focused by optical system 26 on cryogen cooled surface 24. Detector 24 was a 1 mm$^2$ liquid nitrogen cooled detector 24, model MDD-10E0-S1, manufactured by Cincinnati Electronics of Mason, Ohio. The infrared was optically filtered at a cold stop using a 10.6–14 micron bypass filter. Because the infrared absorption coefficient of water in this range is approximately 60 mm$^{-1}$, it is expected that contributions to the infrared signal would originate predominately from superficial depths in the comb, namely in the upper 16 microns.

Detector 24 was placed at a focal plane of 25 millimeter diameter f/1 GE lens 26 configured for unit magnification. The pupil of the lens in system 26 was stopped to 5 mm in diameter, and the infrared signal was amplitude modulated by turning detector 24 on and off with a highly stable synthesized function generator 28 at the rate of approximately 25 kHz to improve the signal-to-noise ratio. The modulated signal from detector 24 was synchronously detected by a lock-in amplifier 30 at the 25 kHz modulation frequency. The output signal from lock-in amplifier 30 was then used to define a threshold trigger for digital delay generator 22 coupled to amplifier 30 through line 32. The output display of detector 24 was also displayed through oscilloscope 34.

Infrared detection system of FIG. 1 was calibrated by measuring the lock-in amplifier's output voltage as a function of the surface temperature of an aluminum block coated with a highly emissive black paint, ε approximately equal to 0.97, specifically, TC-303 black manufactured by GIE Corporation, Provo, Utah. The aluminum calibration block (not shown) was heated by a resistive element from 23° C. to 75° C. The surface temperature of the aluminum block was measured using a precision thermistor attached to the block. The output voltage from the detector varied linearly with temperature.

The foregoing radiometric measurement system is set forth for the purposes of example only and was described as the system used to actually demonstrate the invention. However, it is expressly included that the disclosed radiometer 24, lock-in amplifier 30, function generator 28 and oscilloscope 34 would be deleted and replaced by any one of several currently available commercial radiometers alone or in combination with other conventional monitoring devices that had the response time and sensitivity sufficient to provide the feedback signal consistent with the teachings of the invention.

During irradiation of the in vivo model, when the radiometric surface temperature reached the specified threshold, $T_{thresh}$, ranging between approximately 36 and 41° C., a cryogen spurt was delivered from valve 18 onto comb surface 16. In this way, repetitive pulsed cryogen spray cooling during continuous laser irradiation was accomplished through a feedback system.

Following each experiment, irradiated and cooled sites 14 and 24, respectively, were examined grossly for surface protection by the cryogenic spray cooling, while opposing sides of the combs are checked for blanching due to laser induced photocoagulation. Chickens were euthanized at various times between one hour to 21 days following the experiments as listed in Table II and the combs removed for histologic analysis.

Figure 2:
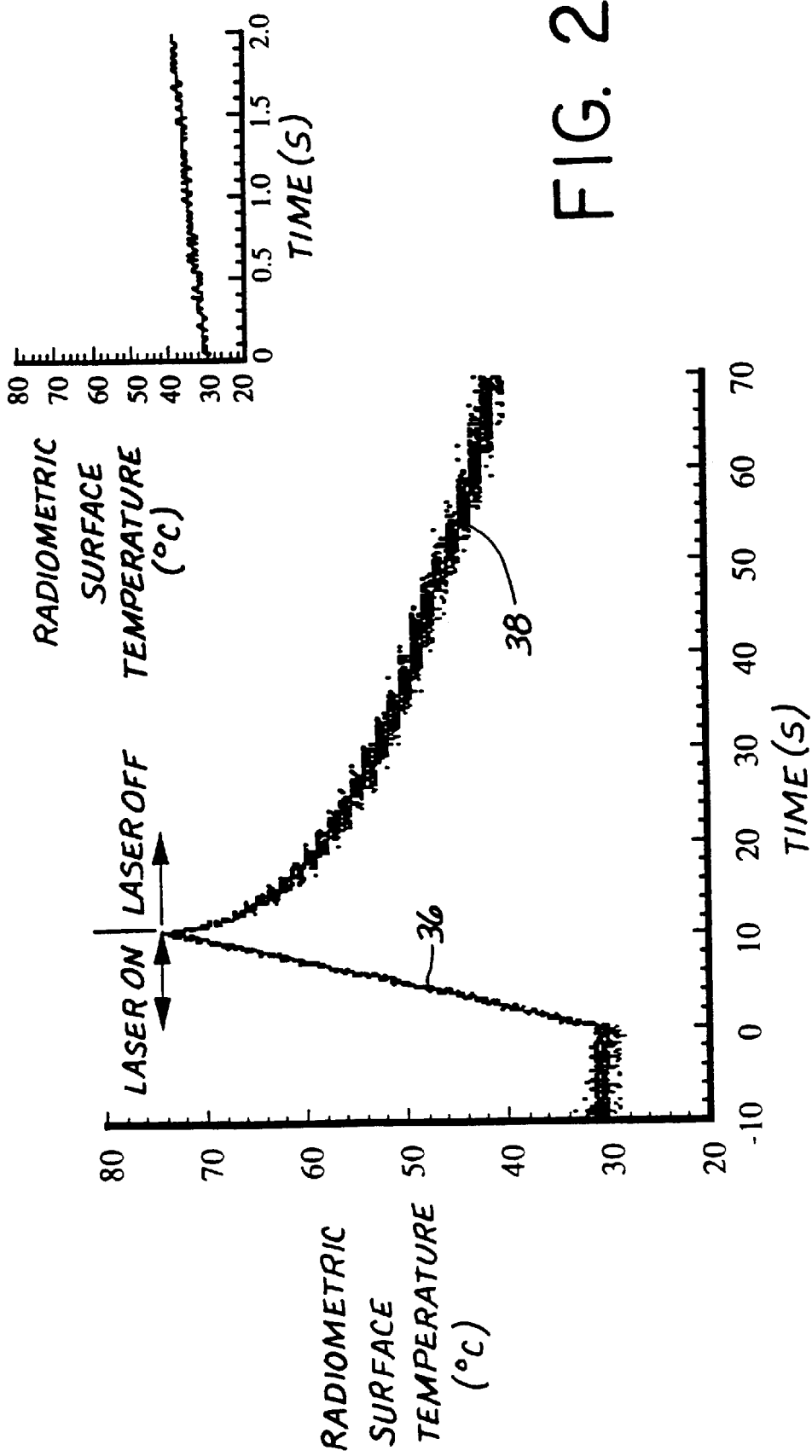
FIG. 2 is a graph of the radiometric surface temperature as a function of time for a 10 second laser irradiation without cryogen spray cooling having a graph inset showing an expansion of the first two seconds of irradiation depicting the linear rate of temperature increase.

FIG. 2 is a graph showing the radiometric surface temperature of detector 24 in degree Celsius on the vertical axis with the horizontal axis showing the time in seconds with the zero time marking the beginning of the laser irradiation. FIG. 2 illustrates the recorded temperature measurement in response to laser radiation of 20 watts with a radiation time of 10 seconds without cryogenic cooling. The response is linear as shown by curve 36 from t=0, the beginning of a irradiation to 10 seconds when the laser is turned off, which in the target illustrated in FIG. 2 heated the comb surface to about 75° C. The inset in FIG. 2 shows a laser induced temperature increase over the first two seconds of radiation in expanded scale, which was about 5° C./sec. Once laser 10 was turned off, the surface temperature decreased monotonically as depicted by curve 38. The comb surface cooled to its initial value after approximately one minute.

Figure 3A:
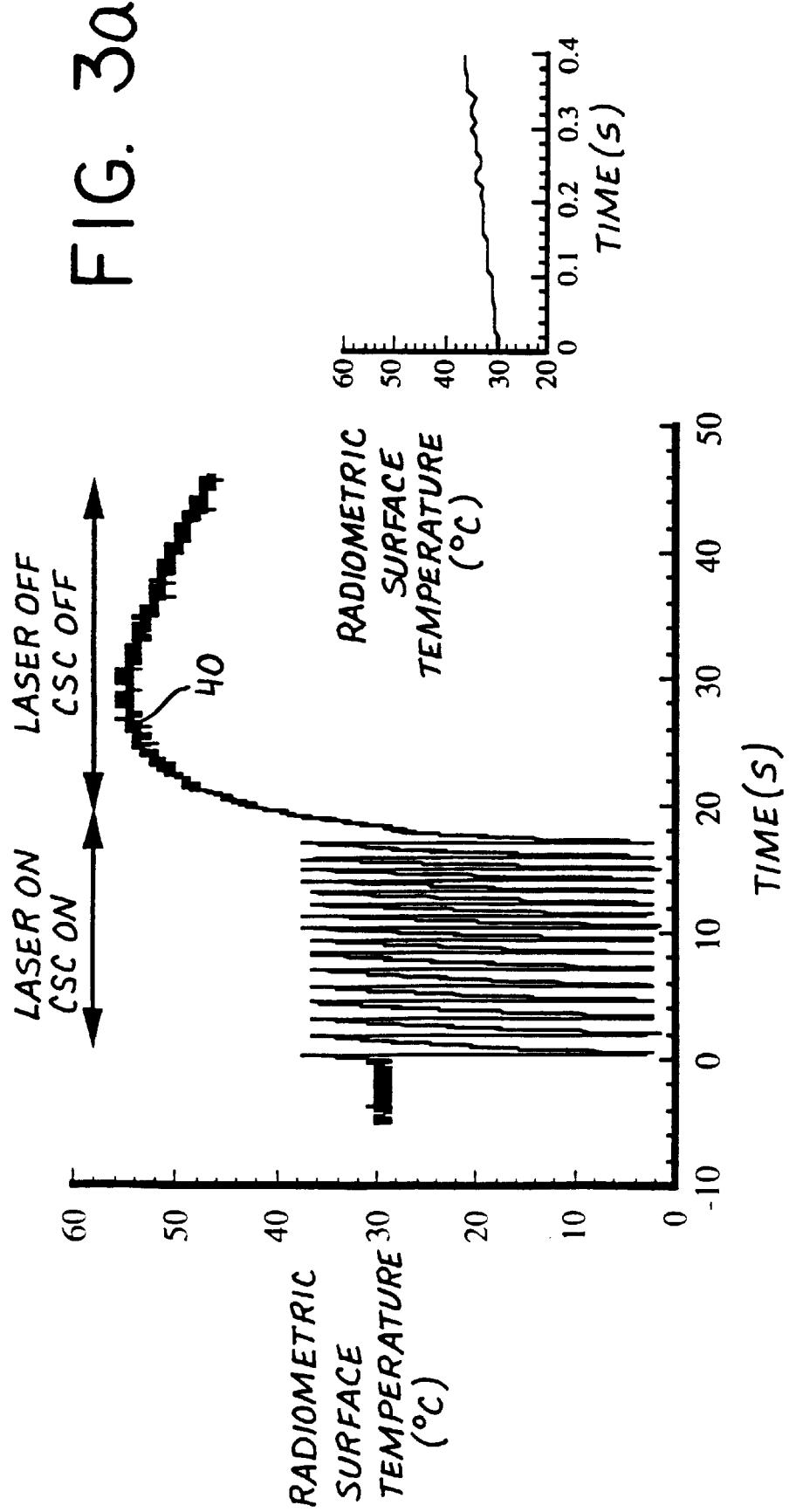
FIG. 3a is a graph of radiometric surface temperature as a function of time showing the temperature with pulse cryogen spray cooling while continuous laser irradiation occurs followed by cessation of both radiation and cryogen spray cooling with a graph inset showing the first 0.4 seconds of time after initiation of irradiation.

Rapid surface temperature reductions to approximately 2° C. were observed in response to chlorodifluoromethane spurts of 50 ms duration sprayed onto comb surface 16 during a laser radiation at 40 watts within a radiation interval of 20 seconds utilizing a temperature threshold of 36° C. as depicted in FIG. 3a. FIG. 3a is a graph showing the radiometric surface temperature of the comb in the vertical scale with time in seconds shown on the horizontal scale, t=0 being the time at which laser 10 was turned on with cryogenic spray cooling and 20 seconds being the time during which laser 10 and the cryogenic cooling was turned off. The inset in FIG. 3a shows the heating rate over the first 0.4 seconds and illustrates a rate of temperature increase of approximately 15° C./sec which resulted due to application of a higher irradiation power of 40 watts.

Figure 3B:
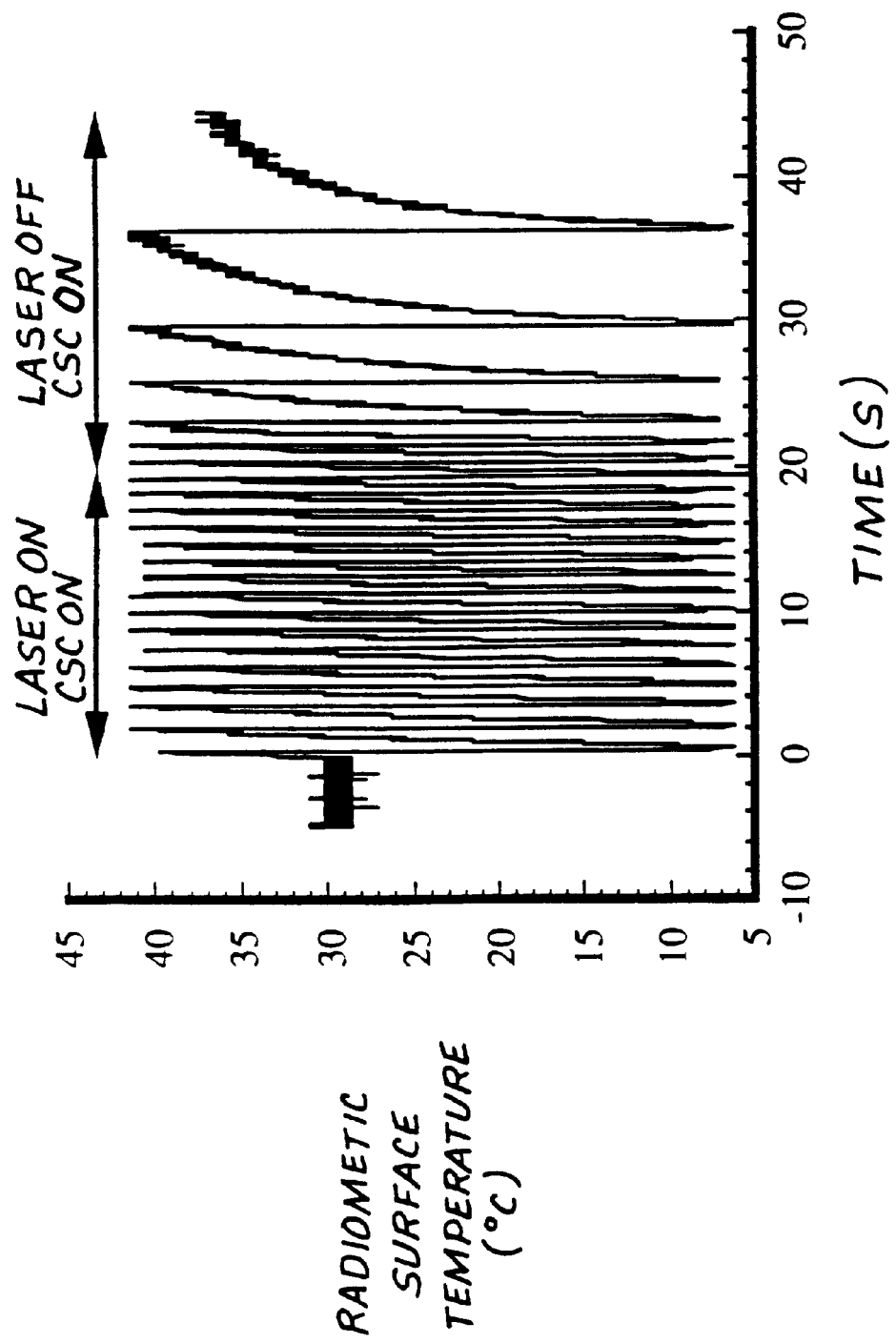
FIG. 3b is a graph of radiometric surface temperature as a function of time showing the temperature with pulse cryogen spray cooling during the continuous irradiation by the laser and thereafter pulse cryogenic cooling at a variable pulse rate after laser irradiation.

Following laser radiation for 20 seconds, heat from within the comb diffused to the surface as illustrated by the rising portion of curve 40. When the feedback system was turned off to prevent post-irradiation spurts, surface temperature response to heat diffusion from within the comb increased to about 55° C. However, when the feedback system was turned on, cryogenic spurts with decreasing frequency were delivered in response to heat diffusion from within the comb to the surface as illustrated in FIG. 3b. FIG. 3b is a graph of the radiometric surface temperature plotted against time under the same conditions in FIG. 3a, but during which the cryogenic spray cooling was continued after laser 10 was turned off. With the threshold temperature set to 40° C. for threshold temperature for the delivery of the cryogen as depicted in FIG. 3b, the graph of FIG. 3b illustrates that 50 ms chlorodifluoromethane spurts consistently induced temperature decreases of 34° C.

When using laser irradiation parameters specified in Table II the irradiated combs always blanched in the absence of cryogen spray cooling. Gross observations of the comb surface showed that no tissue blanching occurred at cryogen spray cooled sites which were maintained at a temperature below the necessary threshold required for thermal damage. However, on the opposite side of the comb with respect to certain ones of the sites where the irradiation at 35 watts for 20 seconds and 40 watts for 30 seconds occurred on the exposed side of the comb, blanching was observed indicating a sufficient laser induced temperature increase was obtained at these locations to cause thermal damage. Whether blanching on the opposing side of the comb could be observed or not was also dependent upon the thickness of the tissue, the thicker tissues when combined with insufficient laser energy showing no evidence of blanching.

Histological observations of a control site which was non-irradiated and non-cooled showed that the normal chicken comb composite structure consisted of epidermis, papillary, and reticular dermis. Multiple venules, having different lumen diameters were present in the dermis. An histological section obtained through a site irradiated in the absence of cryogen spray cooling at 20 watts for 10 seconds, showed detachment of the epidermis in response to the laser irradiation.

Histological sections of the combs were irradiated in conjunction with cryogen spray cooling and showed that the epidermis remained intact with the papillary and reticular dermis clearly distinguished. Most of the dermal venules were occluded and the necrotic tissue appeared as a homogeneous structure. Histological observation generally indicated that cryogen spray cooling was effective in protecting the epidermis and papillary dermis from thermal injury while achieving photocoagulation of deeper tissue.

With chlorodifluoromethane as the cryogen, protection of superficial tissues was achieved when irradiating the comb surface 16 at low and intermediate power levels. However, the opposite side of the comb was not blanched at low power levels where the minimum thickness of the tissue was 5.5 mm except when using power 20 watts for 25 seconds on a tissue thickness of 5.3 mm. The thickest comb site that was blanched on the opposite surface in response to intermediate irradiation was 6.1 mm at 50 watts for 20 seconds duration.

When irradiating the combs at higher power levels of 60 watts for 15 seconds duration superficial tissues were protected. The thickest comb site that was blanched on the opposite side in response to high powered laser irradiation was 7.5 mm at 90 watts for 15 seconds exposure. However, in this particular case protection of superficial tissues was not obtained. Protection may have been afforded with a lower threshold or alternative choice of cryogen.

With tetrafluoroethane as the cryogen, protection of superficial tissues was achieved when irradiating comb surfaces at 5 and 10 watts. However, with these power levels and their corresponding irradiation times as given in Table I, the opposite surfaces of the combs with the smallest thickness being 5.2 mm were not blanched. Protection of superficial tissues was not possible when irradiating combs at 15 watts while cryogen spray cooling with tetrafluoroethane. The thickest comb site that was blanched on the opposite surface was 4.8 mm at 20 watts in 15 seconds duration.

Consider now the theoretical predictions for the observed linear surface temperature increase due to laser irradiation in the absence of cryogenic spray cooling as shown in FIG. 2 and the temperature dependence on the frequency of cryogenic spurts during and after laser irradiation as shown in FIGS. 3a, b and 4. Laser induced temperature increases within the tissue can be computed by solving the heat diffusion equation, which in one dimension is given by $$\frac{\partial^2 \Delta T_L(z, t)}{\partial z^2} + \frac{Q_L(z)}{k} = \frac{1}{\alpha} \frac{\partial \Delta T_L(z, t)}{\partial t} \quad (1)$$

Where $\Delta T_L$(° C.) is the temperature increase, z is the distance in the tissue from the origin of the tissue surface, t is the elapsed time, $\alpha$ and k are tissue thermal diffusivity and conductivity respectively, and $Q_L$ is the volumetric heat production due to absorption of laser radiation. $Q_L$ is assumed to be distributed as $$Q_L(z) = \mu_a A_o exp(-\mu_{eff} z) \quad (2)$$

where $A_o$ is the product of tissue absorption coefficient, irradiance, and a factor that accounts for augmentation of laser fluence rate at the surface due to back-scattering of light inside the tissue, $\mu_a$ is the tissue absorption coefficient and $\mu_{eff}$ is a coefficient that accounts for photon absorption and scattering. Assuming a uniform initial temperature distribution in a semi-infinite medium, and thermally insulated boundary condition at the surface, the solution to equation (1) evaluated as z=0 is $$\Delta T(z=0, t) = \frac{A_0}{k\mu^2_{ef}f}\left[\frac{2\tilde{\mu}_{ef}f}{\sqrt{\pi}} - 1 + P(\tilde{\mu}_{eff})\right] \quad (3)$$

where $\mu_{ff}=\mu_{eff}\sqrt{\alpha t}$, $P(\mu_{ef}f)=e^{\tilde{\mu}_{ef}f^2}\text{erfc}(\mu_{eff})$, with erfc being the complementary error function, 1−erf(x). When $\mu<<1$, it can be shown that equation (3) reduces to $$\Delta T_L(z=0, t) = \frac{A_0\tilde{\mu}2}{k\mu^2_{ef}f} = \frac{A_0\alpha}{k}t \quad (4)$$

Equation (4) indicates that surface temperature increases linearly with time in the absence of cryogen spray cooling as observed in FIG. 2. Equation (4) also shows that surface temperature is directly related to irradiance, tissue thermal properties and absorption coefficient.

To maintain thermal equilibrium at the surface, heat removed by cryogen spray cooling, $q_{csc}(t)$, must equal laser induced thermal flux $q_L(t)$ and hence $$f_{spurt}\alpha q_L(t) \quad (5)$$

where an empirical coefficient C may be used to convert the proportionality to an equality.

Figure 4:
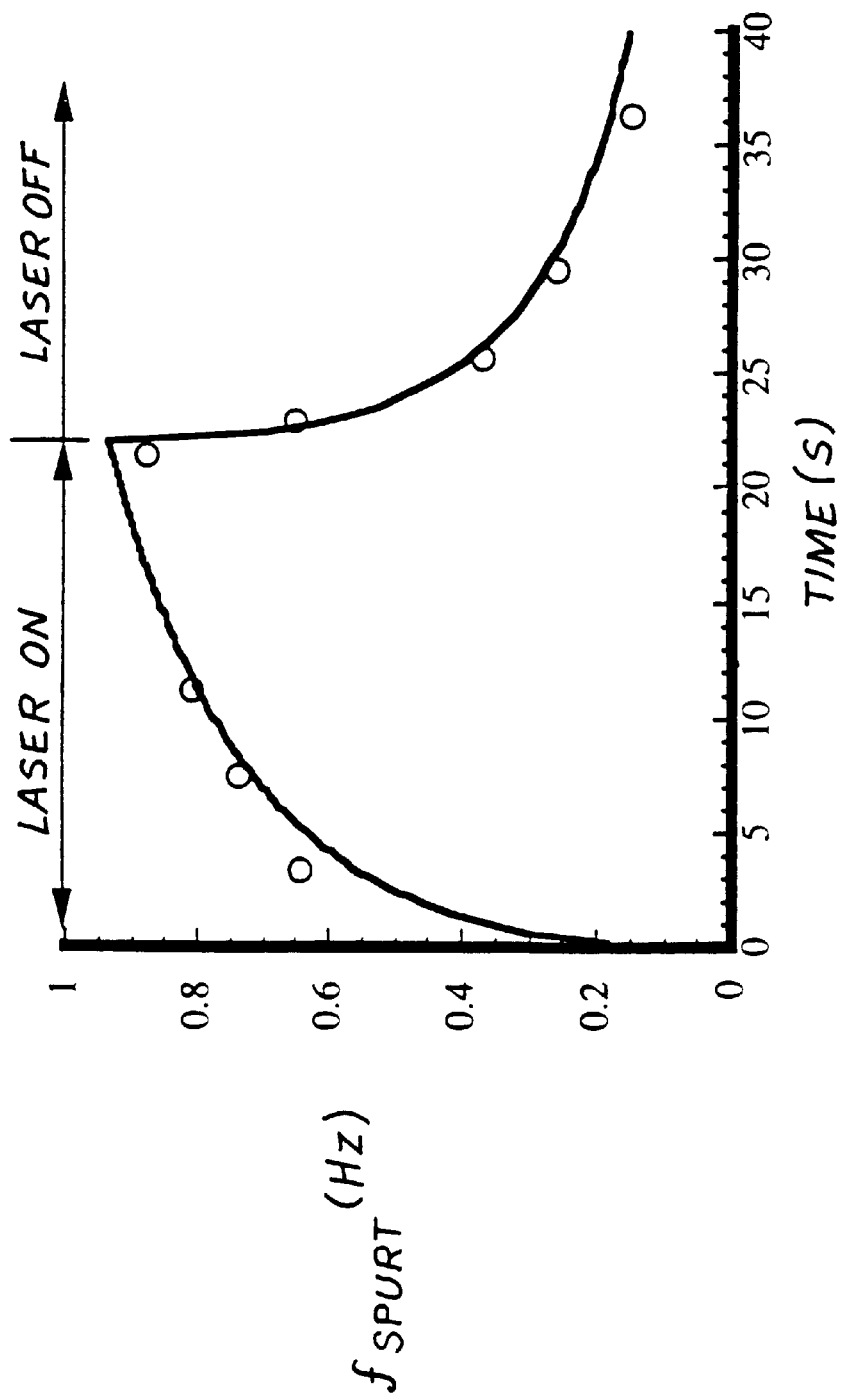
FIG. 4 is a graph of the frequency of cryogen spurts or pulses applied to the skin as a function of time during and after laser irradiation, which are theoretically computed on a solid curve and shown in experimental data as circles, when cryogen spurt rate is controlled to maintain a net zero thermal flux at the surface of the irradiation site.

An analytical expression for $q_L(t)$ is obtained for solving equation (1) and then evaluating the temperature gradient at z=0. Henceforth, $f_{spurt}=C[1-P(\mu_{ef}f)]$ for $t \leq t_{irrad}$ $f_{spurt}=C[P(\mu_{ef}f^*)-P(\mu_{ef}f)]$ for $t \geq t_{irrad}$ where $\mu_{ef}f^*=\mu_{eff}\sqrt{\alpha(t-t_{irrad})}$, $t_{irrad}$ being the duration of cooling. Reasonably good agreement between theoretical and experimental values of $f_{spurt}$ is obtained using $\mu_{ef}f=690$ m$^{-1}$, $\alpha=1.4\cdot10^{-7}$ m$^2\cdot$s$^{-1}$ which is the value for highly vascular tissue such as liver, and C=1.5 m$^2\cdot$J$^{-1}$. The experimental results represent the average value of $f_{spurt}$ over various time intervals during and after irradiation as depicted in the graph of FIG. 4 wherein in the spurt frequency is graphed against time at a 40 watt power exposure for 20 seconds. Similar graph fits can be obtained by changing $\mu$ and $\alpha$ independently by 50% and adjusting C.

As demonstrated in the in vivo experiments using chicken comb as an animal model, epidermis protection and deep tissue photocoagulation is achieved by repetitive applications of a short cryogen spurt during continuous laser irradiation. In addition to protecting the superficial tissue structures from thermal injury, cryogen spray cooling can potentially reduce the irradiation time during laser treatment of hemangiomas. Relatively high incident powers that might otherwise result in photothermal destruction of the superficial tissues, can be applied over times ranging in the tens of seconds, typically 10 to 20 seconds.

Although these experiments show that up to approximately 7 mm of tissue can be coagulated, successful treatment of hemangiomias can be achieved by inducing smaller coagulation depths to initiate the involution process. Results of clinical studies using repetitive pulsed cryogen spray cooling in conjunction with continuous Nd:YAG laser irradiation for treatment of hemangiomas according to the teachings of the invention will provide substantiation of the methodology.

Therefore, it has been demonstrated by the foregoing experiments that spatially selective photocoagulation of subsurface targeted blood vessels by repetitive applications of a short cryogen spurt during continuous laser irradiation is feasible and successful. This procedure is effective in the treatment of thick hemangiomas which requires photocoagulation of subsurface blood vessels while protecting the epidermis and in other applications requiring deep photocoagulation of tissues which superficial tissue protection.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for rapid, spatially confined, deep tissue photocoagulation with protection of superficial tissues comprising:

continuously irradiating a selected tissue site to raise its temperature;

monitoring a biological parameter of said tissue site;

concurrently cooling said tissue site while irradiating and monitoring said tissue site, wherein said cooling is pulsed during irradiation of said tissue site and for a predetermined time thereafter; and controlling said pulsed cooling based on said monitored biological parameter at said tissue site at least during irradiation of said tissue site.

2. The method of claim 1 wherein said cooling is by cryogenic spray cooling.

3. The method of claim 2 where monitoring said biological parameter comprises monitoring a surface temperature at said tissue site.

4. The method of claim 3 where monitoring said surface temperature comprises radiometrically monitoring said surface temperature.

5. The method of claim 1 where irradiating said tissue site comprises the step of irradiating said tissue site with a laser with a wavelength consistent with targeted chromophores in said tissue.

6. The method of claim 1 where irradiating said tissue site comprises irradiating said tissue site with a microwave source.

7. The method of claim 1 where irradiating said tissue site comprises irradiating said tissue site with ultrasound.

8. The method of claim 2 where controlling said cryogen spray cooling comprises initiating said pulsed cryogen spray cooling whenever said monitored temperature exceeds a predetermined threshold condition.

9. The method of claim 2 where controlling said cryogen spray cooling comprises controlling said pulsed cryogen spray cooling according to a biological feedback parameter.

10. The method of claim 8 wherein said pulsed cryogen spray cooling is pulsed at a rate dependent upon power density.

11. The method of claim 9 wherein said pulsed rate of said cryogen spray cooling is controlled as a first function of time of laser irradiation during irradiation of said tissue site and is controlled by a second function of the time after laser irradiation and of the time of irradiation after irradiation of said tissue site ceases.

12. The method of claim 11 wherein said first function is $C[1-P(\mu_{eff})]$ for $t \leq t_{irrad}$ and wherein second function is $C[P(\mu_{eff}^*)-P(\mu_{eff})]$ for $\geq t_{irrad}$ where $\mu_{eff}^* = \mu_{eff}\sqrt{\alpha(t-t_{irrad})}$, $P(\mu^{eff}) = e^{(\mu_{eff}^2)}\mathrm{erfc}(\mu_{eff})$ where $\mu_{eff} = \mu_{eff}\sqrt{\alpha t}$, $\mu_{eff}$ is the effective attenuation coefficient, $\alpha$ is tissue thermal diffusivity and C is an empirical constant coefficient.

13. A method for thermal mediation of tissue with protection of superficial tissues comprising:

irradiating a selected tissue site to raise its temperature;

monitoring a biological parameter of said tissue site;

concurrently cooling said tissue site while irradiating and monitoring said tissue site, wherein said cooling is pulsed during irradiation of said tissue site in a first mode and wherein said cooling is pulsed after irradiation of said tissue site in a second mode; and controlling said pulsed cooling in at least one of said first and second modes based on said monitored biological parameter at said tissue site at least during irradiation of said tissue site.

* * * * *

UNITED STATES PATENT AND TRADEMARK OFFICE
CERTIFICATE OF CORRECTION

PATENT NO.       : 5,979,454
APPLICATION NO.  : 08/870467
DATED            : November 9, 1999
INVENTOR(S)      : Bahman Anvari et al.

It is certified that error appears in the above-identified patent and that said Letters Patent is hereby corrected as shown below:

At col. 9, line 10, delete "$\mu^2_{ef}f$" and insert -- $\mu^2_{eff}$ --.

At col. 9, line 19, in equation (4), delete "$\mu^2_{ef}f$" and insert -- $\mu^2_{eff}$ --.

At col. 9, line 30, delete "$f_{spurt}\alpha q_L(t)$" and insert -- $f_{spurt} \alpha\ q_L(t)$ --.

At col. 9, line 38, between "$f_{spurt}$" and "C", insert -- = --.

At col. 9, line 40, delete "$P(\mu_{ef}f^*)$" and insert -- $P(_{eff}*)$ --.

At col. 9, line 40, delete "$P(\mu_{ef}f)$" and insert -- $P(_{eff})$ --.

At col. 9, line 41, delete "$\mu_{ef}f^*$" and insert -- $\mu_{eff}*$ --.

At col. 9, line 43, delete "$\mu_{ef}f$" and insert -- $\mu_{eff}$ --.

At col. 9, line 48, delete "in".

At col. 12, line 6 claim 12, delete "$P(\mu_{eff})$" and insert -- $P(_{eff})$ --.

At col. 12, line 7 claim 12, delete "$(\mu_{eff}*)$" and insert -- $(_{eff}*)$ --.

At col. 12, line 7 claim 12, delete "$P(\mu_{eff})$" and insert -- $P(_{eff})$ --.

At col. 12, line 7 claim 12, after "for", insert -- t --.

UNITED STATES PATENT AND TRADEMARK OFFICE
CERTIFICATE OF CORRECTION

PATENT NO. : 5,979,454
APPLICATION NO. : 08/870467
DATED : November 9, 1999
INVENTOR(S) : Bahman Anvari et al.

It is certified that error appears in the above-identified patent and that said Letters Patent is hereby corrected as shown below:

At col. 12, line 8 claim 12, delete "$\mu_{eff} = \mu_{eff}$" and insert -- $_{eff} = \mu_{eff}$ --.

Signed and Sealed this

Twentieth Day of January, 2009

JON W. DUDAS
*Director of the United States Patent and Trademark Office*